(12) United States Patent
Atkins et al.

(10) Patent No.: US 11,376,377 B2
(45) Date of Patent: Jul. 5, 2022

(54) CARTRIDGES FOR VAPORIZER DEVICES

(71) Applicant: JUUL Labs, Inc., San Francisco, CA (US)

(72) Inventors: Ariel Atkins, San Francisco, CA (US); Adam Bowen, San Mateo, CA (US); Christopher James Rosser, Cambridge (GB)

(73) Assignee: JUUL Labs, Inc., San Francisco, CA (US)

( * ) Notice: Subject to any disclaimer, the term of this patent is extended or adjusted under 35 U.S.C. 154(b) by 272 days.

(21) Appl. No.: 16/674,449

(22) Filed: Nov. 5, 2019

(65) Prior Publication Data

US 2020/0138112 A1  May 7, 2020

Related U.S. Application Data

(60) Provisional application No. 62/755,889, filed on Nov. 5, 2018.

(51) Int. Cl.
| | |
|---|---|
| *A24F 13/00* | (2006.01) |
| *A24F 17/00* | (2006.01) |
| *A24F 25/00* | (2006.01) |
| *A61M 11/04* | (2006.01) |

(52) U.S. Cl.
CPC ................................ *A61M 11/042* (2014.02)

(58) Field of Classification Search
CPC ...... A24F 40/10; A24F 40/485; A61M 11/042
See application file for complete search history.

(56) References Cited

U.S. PATENT DOCUMENTS

| | | | |
|---|---|---|---|
| 5,019,122 | A | 5/1991 | Clearman et al. |
| 5,020,548 | A | 6/1991 | Farrier et al. |
| 5,042,509 | A | 8/1991 | Banerjee et al. |
| 5,105,831 | A | 4/1992 | Banerjee et al. |
| 5,133,368 | A | 7/1992 | Neumann et al. |
| 7,726,320 | B2 | 6/2010 | Robinson et al. |

(Continued)

FOREIGN PATENT DOCUMENTS

| | | |
|---|---|---|
| CA | 2778786 C | 10/2018 |
| CA | 2949516 C | 6/2019 |

(Continued)

*Primary Examiner* — Abdullah A Riyami
*Assistant Examiner* — Thang H Nguyen
(74) *Attorney, Agent, or Firm* — Mintz Levin Cohn Ferris Glovsky and Popeo, P.C.

(57) ABSTRACT

Cartridges for vaporizer devices are provided. In one exemplary embodiment, the cartridge can include an atomizer and a channel extending through the cartridge from an inlet to an outlet. The atomizer includes a wicking element that is configured to substantially draw a vaporizable material from a reservoir and into the atomizer, and a heating element that is configured to substantially vaporize the vaporizable material into a vaporized material. The channel has an airflow path and a vapor path that intersect at a first junction between the inlet and the outlet. The airflow path is configured to receive and substantially allow air to pass therethrough, and the vapor path is configured to direct the vaporized material into the first junction so that the vaporized material mixes with the air to substantially form an aerosol downstream of the atomizer. Vaporizer devices are also provided.

15 Claims, 6 Drawing Sheets

(56) References Cited

U.S. PATENT DOCUMENTS

| | | | |
|---|---|---|---|
| 8,714,161 B2 | 5/2014 | Liu | |
| 8,794,231 B2 | 8/2014 | Thorens et al. | |
| 9,072,322 B2 | 7/2015 | Liu | |
| 9,101,729 B2 | 8/2015 | Liu | |
| 9,420,829 B2* | 8/2016 | Thorens | H05B 1/0244 |
| 9,687,027 B2* | 6/2017 | Poston | A61M 11/047 |
| 9,844,234 B2 | 12/2017 | Thorens et al. | |
| 9,888,723 B2* | 2/2018 | Cameron | A24F 40/46 |
| 9,999,250 B2 | 6/2018 | Minskoff et al. | |
| 10,285,444 B2 | 5/2019 | Clemens et al. | |
| 10,369,302 B2 | 8/2019 | Suzuki et al. | |
| 10,564,655 B2* | 2/2020 | Blackley | G01N 33/0036 |
| 2003/0150451 A1* | 8/2003 | Shayan | A61M 11/042 128/203.12 |
| 2009/0133691 A1 | 5/2009 | Yamada et al. | |
| 2013/0306064 A1 | 11/2013 | Thorens et al. | |
| 2015/0059780 A1 | 3/2015 | Davis et al. | |
| 2015/0173422 A1 | 6/2015 | Liu | |
| 2015/0335070 A1 | 11/2015 | Sears et al. | |
| 2015/0342255 A1 | 12/2015 | Wu | |
| 2016/0058072 A1 | 3/2016 | Liu | |
| 2016/0120222 A1 | 5/2016 | Bagai et al. | |
| 2017/0027226 A1 | 2/2017 | Mironov et al. | |
| 2017/0065000 A1 | 3/2017 | Sears et al. | |
| 2017/0106153 A1* | 4/2017 | Davidson | A61P 1/00 |
| 2017/0208868 A1 | 7/2017 | Li et al. | |
| 2017/0208870 A1 | 7/2017 | Liu | |
| 2017/0231280 A1 | 8/2017 | Anton | |
| 2017/0238596 A1 | 8/2017 | Matsumoto et al. | |
| 2017/0238605 A1 | 8/2017 | Matsumoto et al. | |
| 2017/0238606 A1 | 8/2017 | Matsumoto et al. | |
| 2017/0238608 A1 | 8/2017 | Matsumoto et al. | |
| 2017/0251727 A1 | 9/2017 | Nielsen | |
| 2017/0265517 A1 | 9/2017 | Swede et al. | |
| 2017/0273360 A1 | 9/2017 | Brinkley et al. | |
| 2017/0318860 A1* | 11/2017 | Adair | A24F 40/485 |
| 2018/0070638 A1* | 3/2018 | Qiu | H02J 7/32 |
| 2018/0110940 A1 | 4/2018 | Suzuki et al. | |
| 2018/0296777 A1 | 10/2018 | Terry et al. | |
| 2019/0124982 A1* | 5/2019 | Atkins | A24F 40/30 |
| 2019/0200679 A1* | 7/2019 | Dayioglu | A24F 40/485 |
| 2019/0343182 A1* | 11/2019 | Yilmaz | A24F 7/00 |
| 2020/0128874 A1 | 4/2020 | Atkins et al. | |
| 2021/0015158 A1* | 1/2021 | Moloney | A24F 40/65 |

FOREIGN PATENT DOCUMENTS

| | | |
|---|---|---|
| CN | 102655773 A | 9/2012 |
| CN | 106102811 A | 11/2016 |
| CN | 207285198 U | 5/2018 |
| EP | 0336457 A2 | 10/1989 |
| EP | 2606756 A1 | 6/2013 |
| EP | 2493341 B1 | 7/2013 |
| EP | 2787847 B1 | 4/2016 |
| EP | 3272239 B1 | 6/2019 |
| KR | 101600646 B1 | 3/2016 |
| KR | 20170132823 A | 12/2017 |
| KR | 20180083424 A | 7/2018 |
| KR | 101957819 B1 | 3/2019 |
| WO | WO-03068300 A1 | 8/2003 |
| WO | WO-2011050943 A1 | 5/2011 |
| WO | WO-2013083635 A1 | 6/2013 |
| WO | WO-2015066136 A1 | 5/2015 |
| WO | WO-2015153443 A1 | 10/2015 |
| WO | WO-2016028544 A1 | 2/2016 |
| WO | WO-2016154798 A1 | 10/2016 |
| WO | WO-2016174179 A1 | 11/2016 |
| WO | WO-2016202301 A1 | 12/2016 |
| WO | WO-2016202304 A1 | 12/2016 |
| WO | WO-2016208760 A1 | 12/2016 |
| WO | WO-2017057286 A1 | 4/2017 |
| WO | WO-2017060279 A1 | 4/2017 |
| WO | WO-2017068099 A1 | 4/2017 |
| WO | WO-2017185051 A1 | 10/2017 |
| WO | WO-2017207586 A1 | 12/2017 |
| WO | WO-2018130391 A1 | 7/2018 |

\* cited by examiner

CARTRIDGES FOR VAPORIZER DEVICES

CROSS-REFERENCE TO RELATED APPLICATIONS

This application claims priority to U.S. Provisional Patent Application No. 62/755,889 filed on Nov. 5, 2018, and entitled "Cartridges For Vaporizer Devices," the disclosure of which is incorporated herein by reference in its entirety.

TECHNICAL FIELD

The subject matter described herein relates to vaporizer devices, including vaporizer cartridges.

BACKGROUND

Vaporizer devices, which can also be referred to as vaporizers, electronic vaporizer devices, or e-vaporizer devices, can be used for delivery of an aerosol (for example, a vapor-phase and/or condensed-phase material suspended in a stationary or moving mass of air or some other gas carrier) containing one or more active ingredients by inhalation of the aerosol by a user of the vaporizing device. For example, electronic nicotine delivery systems (ENDS) include a class of vaporizer devices that are battery powered and that can be used to simulate the experience of smoking, but without burning of tobacco or other substances. Vaporizer devices are gaining increasing popularity both for prescriptive medical use, in delivering medicaments, and for consumption of tobacco, nicotine, and other plant-based materials. Vaporizer devices can be portable, self-contained, and/or convenient for use.

In use of a vaporizer device, the user inhales an aerosol, colloquially referred to as "vapor," which can be generated by a heating element that vaporizes (e.g., causes a liquid or solid to at least partially transition to the gas phase) a vaporizable material, which can be liquid, a solution, a solid, a paste, a wax, and/or any other form compatible for use with a specific vaporizer device. The vaporizable material used with a vaporizer device can be provided within a cartridge for example, a separable part of the vaporizer device that contains vaporizable material) that includes an outlet (for example, a mouthpiece) for inhalation of the aerosol by a user.

To receive the inhalable aerosol generated by a vaporizer device, a user may, in certain examples, activate the vaporizer device by taking a puff, by pressing a button, and/or by some other approach. A puff as used herein can refer to inhalation by the user in a manner that causes a volume of air to be drawn into the vaporizer device such that the inhalable aerosol is generated by a combination of the vaporized vaporizable material with the volume of air.

A vaporizer device typically uses an atomizer that heats the vaporizable material and delivers an inhalable aerosol instead of smoke. The atomizer is placed in line with the primary airflow through the vaporizer device so that the heated vaporizable material can condense within the atomizer to produce the aerosol. As such, the heating, vaporizing, and condensing of the vaporizable material all occur within the atomizer. This can inhibit independent control the condensing of the vaporized vaporizable material separate from that of the airflow. In fact, the condensation conditions would greatly depend on the inhalation profile of the user. Further, the primary airflow can cool the atomizer as it passes along the atomizer, thereby reducing the effectiveness of the vaporizer device to vaporize a desired amount of vaporizable material, such as when a user takes a puff on the vaporizer device. As such, improved vaporizer devices and/or vaporizer cartridges that improve upon or overcome these issues are desired.

SUMMARY

Aspects of the current subject matter relate to vaporizer devices and to cartridges for use in a vaporizer device.

In some variations, one or more of the following features may optionally be included in any feasible combination.

In one exemplary embodiment, a cartridge for a vaporizer device is provided and includes an atomizer and a channel extending through the cartridge from an inlet to an outlet. The atomizer includes a wicking element that is configured to substantially draw a vaporizable material from a reservoir and into the atomizer, and a heating element that is configured to substantially vaporize the vaporizable material into a vaporized material. The channel has an airflow path and a vapor path that intersect at a first junction between the inlet and the outlet, the airflow path being configured to receive and substantially allow air to pass therethrough. The atomizer is in communication with the vapor path such that the vaporized material flows into the vapor path, and the vapor path is configured to direct the vaporized material into the first junction so that the vaporized material mixes with the air to substantially form an aerosol downstream of the atomizer.

In some embodiments, the first junction is a T-junction. In some embodiments, the aerosol can be substantially formed at the first junction.

The airflow path can have a variety of configurations. For example, in some embodiments, the airflow path can include a first airflow path segment and a second airflow path segment, in which the first airflow path segment can be in communication with the atomizer. The first airflow path and the second airflow path segment can intersect at a second junction that can be upstream of the first junction, in which the second junction substantially diverts a first portion of the air into the first airflow path segment and across the atomizer, and the second junction can further divert a second portion of the air towards the first junction. The second junction can be a T-junction. The first portion of the air can be configured to substantially transport the vaporized material from the atomizer and into the first junction. The first portion of air can have a first volume and the second portion of air can have a second volume that is greater than the first volume.

In some embodiments, a portion of the airflow path that is downstream of the first junction can be configured to substantially allow the aerosol to pass therethrough and out of the channel.

In another exemplary embodiment, a cartridge for a vaporizer device is provided and includes an airflow channel and an atomizer. The airflow channel defines an airflow path that extends through the cartridge, in which the airflow path is configured to receive and substantially allow air to flow into and through the airflow channel. The atomizer includes a wicking element that is configured to substantially draw a vaporizable material from a reservoir and into the atomizer, a heating element that is configured to substantially vaporize the vaporizable material into a vaporized material, and a vapor chamber that is in communication with the wicking element and the airflow channel. The vapor chamber is configured to substantially allow at least a portion of the vaporized material to pass therethrough and into the airflow channel so that the portion of the vaporized material mixes with the air to form an aerosol outside of the atomizer.

The vapor chamber can have a variety of configurations. For example, in some embodiments, at least a portion of the vapor chamber can be bounded by the airflow channel, in which the portion of the vapor chamber can be formed of a permeable material that can be configured to allow the vaporized material to substantially pass therethrough and into the airflow path. In other embodiments, the vapor chamber can include at least one vent that extends between the vapor chamber and the airflow channel, in which the at least one vent can be configured to substantially direct the vaporized material from the vapor chamber and into the airflow path. In such embodiments, a velocity of the air flowing adjacent to the at least one vent can substantially create a pressure differential across the at least one vent and between the vapor chamber and the airflow channel.

The wicking element can have a variety of configurations. For example, in some embodiments, the wicking element can extend from a first surface to an opposing second surface, in which the first surface and second surface can each extend substantially parallel to the airflow path. The heating element can direct heat across a lateral surface of the wicking element extending between the first and second surfaces. The lateral surface can be interposed between a bulk of the wicking element and the vapor chamber.

In another exemplary embodiment, a vaporizer device is provided and includes a vaporizer body and a cartridge that is selectively coupled to and removable from the vaporizer body. The cartridge includes an atomizer and a channel extending through the cartridge from an inlet to an outlet. The atomizer can include a wicking element that is configured to substantially draw a vaporizable material from a reservoir and into the atomizer, and a heating element that is configured to substantially vaporize the vaporizable material into a vaporized material. The channel having an airflow path and a vapor path that intersect at a first junction between the inlet and the outlet, in which the airflow path can be configured to receive and substantially allow air to pass therethrough. The atomizer is in communication with the vapor path such that the vaporized material flows into the vapor path, and the vapor path is configured to direct the vaporized material into the first junction so that the vaporized material mixes with the air to substantially form an aerosol downstream of the atomizer.

In some embodiments, the vaporizer body can include a power source.

The airflow path can have a variety of configurations. For example, in some embodiments, the airflow path can include a first airflow path segment and a second airflow path segment, in which the first airflow path segment can be in communication with the atomizer. The first air flow path segment and the second airflow path segment can intersect at a second junction that is upstream of the first junction, in which the second junction can substantially divert a first portion of the air into the first airflow path segment and across the atomizer, and the second junction can further divert a second portion of the air towards the first junction.

The details of one or more variations of the subject matter described herein are set forth in the accompanying drawings and the description below. Other features and advantages of the subject matter described herein will be apparent from the description and drawings, and from the claims. The claims that follow this disclosure are intended to define the scope of the protected subject matter.

BRIEF DESCRIPTION OF THE DRAWINGS

The accompanying drawings, which are incorporated into and constitute a part of this specification, show certain aspects of the subject matter disclosed herein and, together with the description, help explain some of the principles associated with the disclosed implementations. In the drawings:

FIG. 1A is a block diagram of a vaporizer device;

FIG. 1B is a top view of an embodiment of a vaporizer device, showing a vaporizer cartridge separated from a vaporizer device body;

FIG. 1C is a top view of the vaporizer device of FIG. 1B, showing the vaporizer cartridge coupled to the vaporizer device body;

FIG. 1D is a perspective view of the vaporizer device of FIG. 1C;

FIG. 1E is a perspective view of the vaporizer cartridge of FIG. 1B;

FIG. 1F is another perspective view of the vaporizer cartridge of FIG. 1E;

FIG. 2 illustrates a schematic of another embodiment of a vaporizer cartridge;

FIG. 3 illustrates a schematic of another embodiment of a vaporizer cartridge;

FIG. 4 illustrates a schematic of another embodiment of a vaporizer cartridge; and FIG. 5 illustrates a schematic of another embodiment of a vaporizer cartridge.

When practical, similar reference numbers denote similar structures, features, or elements.

DETAILED DESCRIPTION

Implementations of the current subject matter include methods, apparatuses, articles of manufacture, and systems relating to vaporization of one or more materials for inhalation by a user. Example implementations include vaporizer devices and systems including vaporizer devices. The term "vaporizer device" as used in the following description and claims refers to any of a self-contained apparatus, an apparatus that includes two or more separable parts (for example, a vaporizer body that includes a battery and other hardware, and a cartridge that includes a vaporizable material), and/or the like. A "vaporizer system," as used herein, can include one or more components, such as a vaporizer device. Examples of vaporizer devices consistent with implementations of the current subject matter include electronic vaporizers, electronic nicotine delivery systems (ENDS), and/or the like. In general, such vaporizer devices are hand-held devices that heat (such as by convection, conduction, radiation, and/or some combination thereof) a vaporizable material to provide an inhalable dose of the material.

The vaporizable material used with a vaporizer device can be provided within a cartridge (for example, a part of the vaporizer device that contains the vaporizable material in a reservoir or other container) which can be refillable when empty, or disposable such that a new cartridge containing additional vaporizable material of a same or different type can be used). A vaporizer device can be a cartridge-using vaporizer device, a cartridge-less vaporizer device, or a multi-use vaporizer device capable of use with or without a cartridge. For example, a vaporizer device can include a heating chamber (for example, an oven or other region in which material is heated by a heating element) configured to receive a vaporizable material directly into the heating chamber, and/or a reservoir or the like for containing the vaporizable material.

In some implementations, a vaporizer device can be configured for use with a liquid vaporizable material (for example, a carrier solution in which an active and/or inactive ingredient(s) are suspended or held in solution, or a liquid form of the vaporizable material itself). The liquid vaporizable material can be capable of being completely vaporized. Alternatively, at least a portion of the liquid vaporizable material can remain after all of the material suitable for inhalation has been vaporized.

Figure 1A:
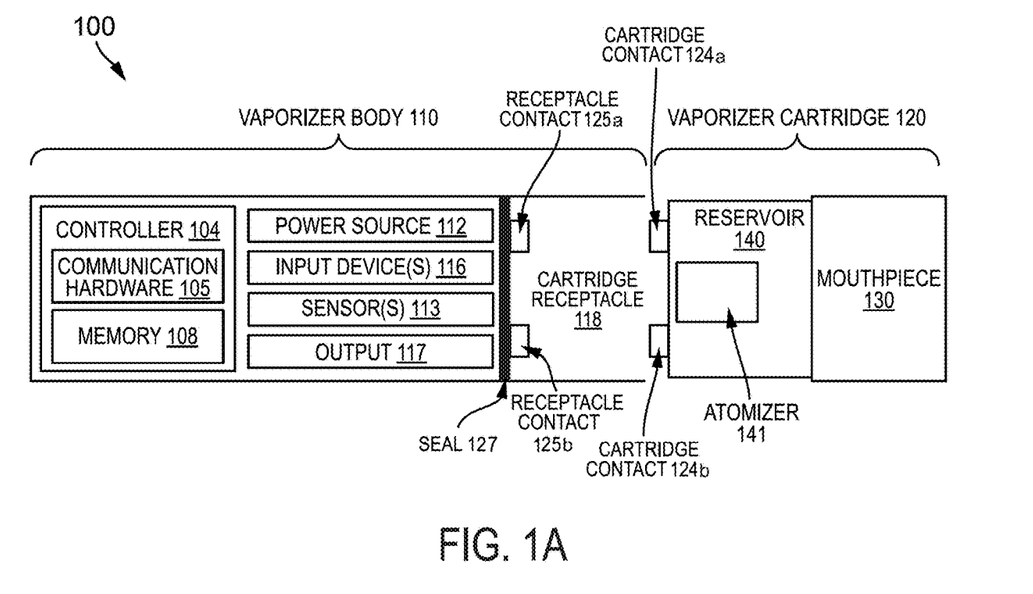

Referring to the block diagram of FIG. 1A, a vaporizer device 100 can include a power source 112 (for example, a battery, which can be a rechargeable battery), and a controller 104 (for example, a processor, circuitry, etc. capable of executing logic) for controlling delivery of heat to an atomizer 141 to cause a vaporizable material 102 to be converted from a condensed form (such as a liquid, a solution, a suspension, a part of an at least partially unprocessed plant material, etc.) to the gas phase. The controller 104 can be part of one or more printed circuit boards (PCBs) consistent with certain implementations of the current subject matter.

After conversion of the vaporizable material 102 to the gas phase, at least some of the vaporizable material 102 in the gas phase can condense to form particulate matter in at least a partial local equilibrium with the gas phase as part of an aerosol, which can form some or all of an inhalable dose provided by the vaporizer device 100 during a user's puff or draw on the vaporizer device 100. It should be appreciated that the interplay between gas and condensed phases in an aerosol generated by a vaporizer device 100 can be complex and dynamic, due to factors such as ambient temperature, relative humidity, chemistry, flow conditions in airflow paths (both inside the vaporizer device and in the airways of a human or other animal), and/or mixing of the vaporizable material 102 in the gas phase or in the aerosol phase with other air streams, which can affect one or more physical parameters of an aerosol. In some vaporizer devices, and particularly for vaporizer devices configured for delivery of volatile vaporizable materials, the inhalable dose can exist predominantly in the gas phase (for example, formation of condensed phase particles can be very limited).

The atomizer 141 in the vaporizer device 100 can be configured to vaporize a vaporizable material 102. The vaporizable material 102 can be a liquid. Examples of the vaporizable material 102 include neat liquids, suspensions, solutions, mixtures, and/or the like. The atomizer 141 can include a wicking element (i.e., a wick) configured to convey an amount of the vaporizable material 102 to a part of the atomizer 141 that includes a heating element (not shown in FIG. 1A).

For example, the wicking element can be configured to draw the vaporizable material 102 from a reservoir 140 configured to contain the vaporizable material 102, such that the vaporizable material 102 can be vaporized by heat delivered from a heating element. The wicking element can also optionally allow air to enter the reservoir 140 and replace the volume of vaporizable material 102 removed. In some implementations of the current subject matter, capillary action can pull vaporizable material 102 into the wick for vaporization by the heating element, and air can return to the reservoir 140 through the wick to at least partially equalize pressure in the reservoir 140. Other methods of allowing air back into the reservoir 140 to equalize pressure are also within the scope of the current subject matter.

As used herein, the terms "wick" or "wicking element" include any material capable of causing fluid motion via capillary pressure.

The heating element can include one or more of a conductive heater, a radiative heater, and/or a convective heater. One type of heating element is a resistive heating element, which can include a material (such as a metal or alloy, for example a nickel-chromium alloy, or a non-metallic resistor) configured to dissipate electrical power in the form of heat when electrical current is passed through one or more resistive segments of the heating element. In some implementations of the current subject matter, the atomizer 141 can include a heating element which includes a resistive coil or other heating element wrapped around, positioned within, integrated into a bulk shape of, pressed into thermal contact with, or otherwise arranged to deliver heat to a wicking element, to cause the vaporizable material 102 drawn from the reservoir 140 by the wicking element to be vaporized for subsequent inhalation by a user in a gas and/or a condensed (for example, aerosol particles or droplets) phase. Other wicking elements, heating elements, and/or atomizer assembly configurations are also possible.

The heating element can be activated in association with a user puffing (i.e., drawing, inhaling, etc.) on a mouthpiece 130 of the vaporizer device 100 to cause air to flow from an air inlet, along an airflow path that passes the atomizer 141 (i.e., wicking element and heating element). Optionally, air can flow from an air inlet through one or more condensation areas or chambers, to an air outlet in the mouthpiece 130. Incoming air moving along the airflow path moves over or through the atomizer 141, where vaporizable material 102 in the gas phase is entrained into the air. The heating element can be activated via the controller 104, which can optionally be a part of a vaporizer body 110 as discussed herein, causing current to pass from the power source 112 through a circuit including the resistive heating element, which is optionally part of a vaporizer cartridge 120 as discussed herein. As noted herein, the entrained vaporizable material 102 in the gas phase can condense as it passes through the remainder of the airflow path such that an inhalable dose of the vaporizable material 102 in an aerosol form can be delivered from the air outlet (for example, the mouthpiece 130) for inhalation by a user.

Activation of the heating element can be caused by automatic detection of a puff based on one or more signals generated by one or more of a sensor 113. The sensor 113 and the signals generated by the sensor 113 can include one or more of: a pressure sensor or sensors disposed to detect pressure along the airflow path relative to ambient pressure (or optionally to measure changes in absolute pressure), a motion sensor or sensors (for example, an accelerometer) of the vaporizer device 100, a flow sensor or sensors of the vaporizer device 100, a capacitive lip sensor of the vaporizer device 100, detection of interaction of a user with the vaporizer device 100 via one or more input devices 116 (for example, buttons or other tactile control devices of the vaporizer device 100), receipt of signals from a computing device in communication with the vaporizer device 100, and/or via other approaches for determining that a puff is occurring or imminent.

As discussed herein, the vaporizer device 100 consistent with implementations of the current subject matter can be configured to connect (such as, for example, wirelessly or via a wired connection) to a computing device (or optionally two or more devices) in communication with the vaporizer device 100. To this end, the controller 104 can include communication hardware 105. The controller 104 can also include a memory 108. The communication hardware 105 can include firmware and/or can be controlled by software for executing one or more cryptographic protocols for the communication.

A computing device can be a component of a vaporizer system that also includes the vaporizer device 100, and can include its own hardware for communication, which can establish a wireless communication channel with the communication hardware 105 of the vaporizer device 100. For example, a computing device used as part of a vaporizer system can include a general-purpose computing device (such as a smartphone, a tablet, a personal computer, some other portable device such as a smartwatch, or the like) that executes software to produce a user interface for enabling a user to interact with the vaporizer device 100. In other implementations of the current subject matter, such a device used as part of a vaporizer system can be a dedicated piece of hardware such as a remote control or other wireless or wired device having one or more physical or soft (i.e., configurable on a screen or other display device and selectable via user interaction with a touch-sensitive screen or some other input device like a mouse, pointer, trackball, cursor buttons, or the like) interface controls. The vaporizer device 100 can also include one or more outputs 117 or devices for providing information to the user. For example, the outputs 117 can include one or more light emitting diodes (LEDs) configured to provide feedback to a user based on a status and/or mode of operation of the vaporizer device 100.

In the example in which a computing device provides signals related to activation of the resistive heating element, or in other examples of coupling of a computing device with the vaporizer device 100 for implementation of various control or other functions, the computing device executes one or more computer instruction sets to provide a user interface and underlying data handling. In one example, detection by the computing device of user interaction with one or more user interface elements can cause the computing device to signal the vaporizer device 100 to activate the heating element to reach an operating temperature for creation of an inhalable dose of vapor/aerosol. Other functions of the vaporizer device 100 can be controlled by interaction of a user with a user interface on a computing device in communication with the vaporizer device 100.

The temperature of a resistive heating element of the vaporizer device 100 can depend on a number of factors, including an amount of electrical power delivered to the resistive heating element and/or a duty cycle at which the electrical power is delivered, conductive heat transfer to other parts of the electronic vaporizer device 100 and/or to the environment, latent heat losses due to vaporization of the vaporizable material 102 from the wicking element and/or the atomizer 141 as a whole, and convective heat losses due to airflow (i.e., air moving across the heating element or the atomizer 141 as a whole when a user inhales on the vaporizer device 100). As noted herein, to reliably activate the heating element or heat the heating element to a desired temperature, the vaporizer device 100 may, in some implementations of the current subject matter, make use of signals from the sensor 113 (for example, a pressure sensor) to determine when a user is inhaling. The sensor 113 can be positioned in the airflow path and/or can be connected (for example, by a passageway or other path) to an airflow path containing an inlet for air to enter the vaporizer device 100 and an outlet via which the user inhales the resulting vapor and/or aerosol such that the sensor 113 experiences changes (for example, pressure changes) concurrently with air passing through the vaporizer device 100 from the air inlet to the air outlet. In some implementations of the current subject matter, the heating element can be activated in association with a user's puff, for example by automatic detection of the puff, or by the sensor 113 detecting a change (such as a pressure change) in the airflow path.

The sensor 113 can be positioned on or coupled to (i.e., electrically or electronically connected, either physically or via a wireless connection) the controller 104 (for example, a printed circuit board assembly or other type of circuit board). To take measurements accurately and maintain durability of the vaporizer device 100, it can be beneficial to provide a seal 127 resilient enough to separate an airflow path from other parts of the vaporizer device 100. The seal 127, which can be a gasket, can be configured to at least partially surround the sensor 113 such that connections of the sensor 113 to the internal circuitry of the vaporizer device 100 are separated from a part of the sensor 113 exposed to the airflow path. In an example of a cartridge-based vaporizer device, the seal 127 can also separate parts of one or more electrical connections between the vaporizer body 110 and the vaporizer cartridge 120. Such arrangements of the seal 127 in the vaporizer device 100 can be helpful in mitigating against potentially disruptive impacts on vaporizer components resulting from interactions with environmental factors such as water in the vapor or liquid phases, other fluids such as the vaporizable material 102, etc., and/or to reduce the escape of air from the designated airflow path in the vaporizer device 100. Unwanted air, liquid or other fluid passing and/or contacting circuitry of the vaporizer device 100 can cause various unwanted effects, such as altered pressure readings, and/or can result in the buildup of unwanted material, such as moisture, excess vaporizable material 102, etc., in parts of the vaporizer device 100 where they can result in poor pressure signal, degradation of the sensor 113 or other components, and/or a shorter life of the vaporizer device 100. Leaks in the seal 127 can also result in a user inhaling air that has passed over parts of the vaporizer device 100 containing, or constructed of, materials that may not be desirable to be inhaled.

In some implementations, the vaporizer body 110 includes the controller 104, the power source 112 (for example, a battery), one more of the sensor 113, charging contacts (such as those for charging the power source 112), the seal 127, and a cartridge receptacle 118 configured to receive the vaporizer cartridge 120 for coupling with the vaporizer body 110 through one or more of a variety of attachment structures. In some examples, the vaporizer cartridge 120 includes the reservoir 140 for containing the vaporizable material 102, and the mouthpiece 130 has an aerosol outlet for delivering an inhalable dose to a user. The vaporizer cartridge 120 can include the atomizer 141 having a wicking element and a heating element. Alternatively, one or both of the wicking element and the heating element can be part of the vaporizer body 110. In implementations in which any part of the atomizer 141 (i.e., heating element and/or wicking element) is part of the vaporizer body 110, the vaporizer device 100 can be configured to supply vaporizable material 102 from the reservoir 140 in the vaporizer cartridge 120 to the part(s) of the atomizer 141 included in the vaporizer body 110.

In an embodiment of the vaporizer device 100 in which the power source 112 is part of the vaporizer body 110, and a heating element is disposed in the vaporizer cartridge 120 and configured to couple with the vaporizer body 110, the vaporizer device 100 can include electrical connection features (for example, means for completing a circuit) for completing a circuit that includes the controller 104 (for example, a printed circuit board, a microcontroller, or the like), the power source 112, and the heating element (for example, a heating element within the atomizer 141). These features can include one or more contacts (referred to herein as cartridge contacts 124a and 124b) on a bottom surface of the vaporizer cartridge 120 and at least two contacts (referred to herein as receptacle contacts 125a and 125b) disposed near a base of the cartridge receptacle 118 of the vaporizer device 100 such that the cartridge contacts 124a and 124b and the receptacle contacts 125a and 125b make electrical connections when the vaporizer cartridge 120 is inserted into and coupled with the cartridge receptacle 118. The circuit completed by these electrical connections can allow delivery of electrical current to a heating element and can further be used for additional functions, such as measuring a resistance of the heating element for use in determining and/or controlling a temperature of the heating element based on a thermal coefficient of resistivity of the heating element.

In some implementations of the current subject matter, the cartridge contacts 124a and 124b and the receptacle contacts 125a and 125b can be configured to electrically connect in either of at least two orientations. In other words, one or more circuits necessary for operation of the vaporizer device 100 can be completed by insertion of the vaporizer cartridge 120 into the cartridge receptacle 118 in a first rotational orientation (around an axis along which the vaporizer cartridge 120 is inserted into the cartridge receptacle 118 of the vaporizer body 110) such that the cartridge contact 124a is electrically connected to the receptacle contact 125a and the cartridge contact 124b is electrically connected to the receptacle contact 125b. Furthermore, the one or more circuits necessary for operation of the vaporizer device 100 can be completed by insertion of the vaporizer cartridge 120 in the cartridge receptacle 118 in a second rotational orientation such cartridge contact 124a is electrically connected to the receptacle contact 125b and cartridge contact 124b is electrically connected to the receptacle contact 125a.

For example, the vaporizer cartridge 120 or at least the insertable end 122 of the vaporizer cartridge 120 can be symmetrical upon a rotation of 180° around an axis along which the vaporizer cartridge 120 is inserted into the cartridge receptacle 118. In such a configuration, the circuitry of the vaporizer device 100 can support identical operation regardless of which symmetrical orientation of the vaporizer cartridge 120 occurs.

In one example of an attachment structure for coupling the vaporizer cartridge 120 to the vaporizer body 110, the vaporizer body 110 includes one or more detents (for example, dimples, protrusions, etc.) protruding inwardly from an inner surface of the cartridge receptacle 118, additional material (such as metal, plastic, etc.) formed to include a portion protruding into the cartridge receptacle 118, and/or the like. One or more exterior surfaces of the vaporizer cartridge 120 can include corresponding recesses (not shown in FIG. 1A) that can fit and/or otherwise snap over such detents or protruding portions when the vaporizer cartridge 120 is inserted into the cartridge receptacle 118 on the vaporizer body 110. When the vaporizer cartridge 120 and the vaporizer body 110 are coupled (e.g., by insertion of the vaporizer cartridge 120 into the cartridge receptacle 118 of the vaporizer body 110), the detents or protrusions of the vaporizer body 110 can fit within and/or otherwise be held within the recesses of the vaporizer cartridge 120, to hold the vaporizer cartridge 120 in place when assembled. Such an assembly can provide enough support to hold the vaporizer cartridge 120 in place to ensure good contact between the cartridge contacts 124a and 124b and the receptacle contacts 125a and 125b, while allowing release of the vaporizer cartridge 120 from the vaporizer body 110 when a user pulls with reasonable force on the vaporizer cartridge 120 to disengage the vaporizer cartridge 120 from the cartridge receptacle 118.

In some implementations, the vaporizer cartridge 120, or at least an insertable end 122 of the vaporizer cartridge 120 configured for insertion in the cartridge receptacle 118, can have a non-circular cross section transverse to the axis along which the vaporizer cartridge 120 is inserted into the cartridge receptacle 118. For example, the non-circular cross section can be approximately rectangular, approximately elliptical (i.e., have an approximately oval shape), non-rectangular but with two sets of parallel or approximately parallel opposing sides (i.e., having a parallelogram-like shape), or other shapes having rotational symmetry of at least order two. In this context, approximate shape indicates that a basic likeness to the described shape is apparent, but that sides of the shape in question need not be completely linear and vertices need not be completely sharp. Rounding of both or either of the edges or the vertices of the cross-sectional shape is contemplated in the description of any non-circular cross section referred to herein.

The cartridge contacts 124a and 124b and the receptacle contacts 125a and 125b can take various forms. For example, one or both sets of contacts can include conductive pins, tabs, posts, receiving holes for pins or posts, or the like. Some types of contacts can include springs or other features to facilitate better physical and electrical contact between the contacts on the vaporizer cartridge 120 and the vaporizer body 110. The electrical contacts can optionally be gold-plated, and/or include other materials.

Figure 1B:
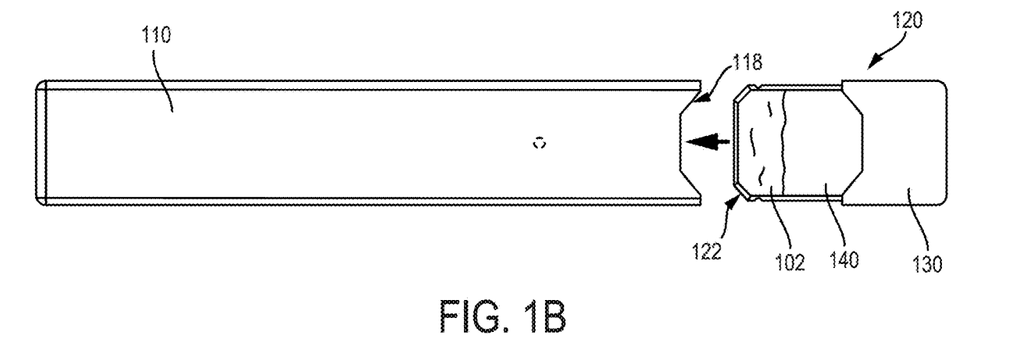
Figure 1C:
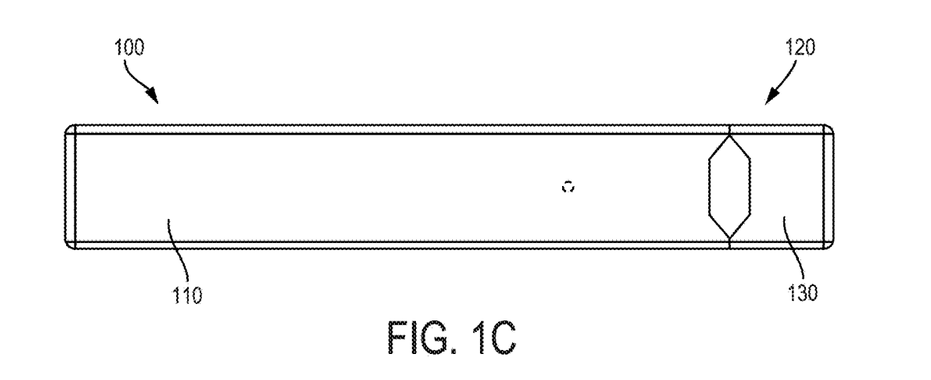
Figure 1D:
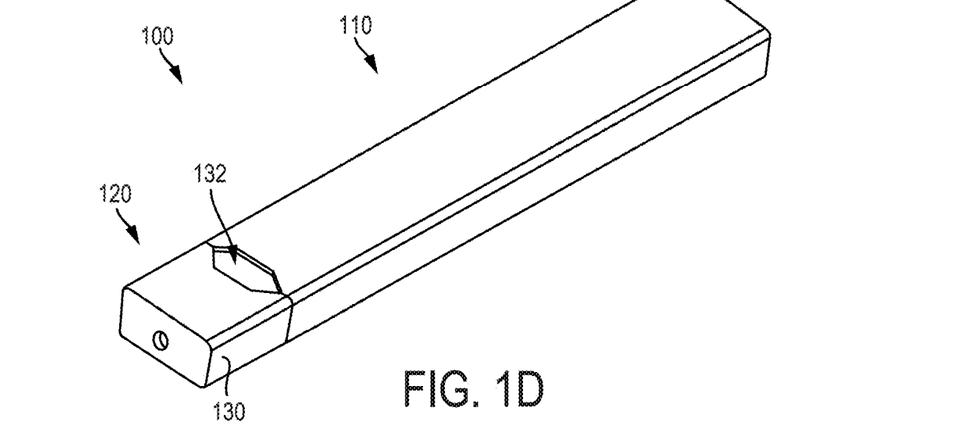

FIGS. 1B-1D illustrate an embodiment of the vaporizer body 110 having a cartridge receptacle 118 into which the vaporizer cartridge 120 can be releasably inserted. FIGS. 1B and 1C show top views of the vaporizer device 100 illustrating the vaporizer cartridge 120 being positioned for insertion and inserted, respectively, into the vaporizer body 110. FIG. 1D illustrates the reservoir 140 of the vaporizer cartridge 120 being formed in whole or in part from translucent material such that a level of the vaporizable material 102 is visible from a window 132 (e.g., translucent material) along the vaporizer cartridge 120. The vaporizer cartridge 120 can be configured such that the window 132 remains visible when insertably received by the vaporizer cartridge receptacle 118 of the vaporizer body 110. For example, in one exemplary configuration, the window 132 can be disposed between a bottom edge of the mouthpiece 130 and a top edge of the vaporizer body 110 when the vaporizer cartridge 120 is coupled with the cartridge receptacle 118.

Figure 1E:
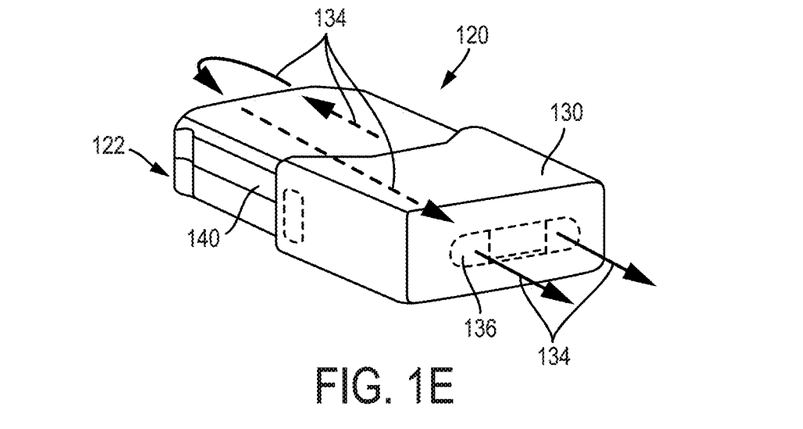

FIG. 1E illustrates an example airflow path 134 created during a puff by a user on the vaporizer device 100. The airflow path 134 can direct air to a vaporization chamber 150 (see FIG. 1F) contained in a wick housing where the air is combined with inhalable aerosol for delivery to a user via a mouthpiece 130, which can also be part of the vaporizer cartridge 120. For example, when a user puffs on the vaporizer device 100 device 100, air can pass between an outer surface of the vaporizer cartridge 120 (for example, window 132 shown in FIG. 1D) and an inner surface of the cartridge receptacle 118 on the vaporizer body 110. Air can then be drawn into the insertable end 122 of the vaporizer cartridge 120, through the vaporization chamber 150 that includes or contains the heating element and wick, and out through an outlet 136 of the mouthpiece 130 for delivery of the inhalable aerosol to a user.

As shown in FIG. 1E, this configuration causes air to flow down around the insertable end 122 of the vaporizer cartridge 120 into the cartridge receptacle 118 and then flow back in the opposite direction after passing around the insertable end 122 (e.g., an end opposite of the end including the mouthpiece 130) of the vaporizer cartridge 120 as it enters into the cartridge body toward the vaporization chamber 150. The airflow path 134 then travels through the interior of the vaporizer cartridge 120, for example via one or more tubes or internal channels (such as cannula 128 shown in FIG. 1F) and through one or more outlets (such as outlet 136) formed in the mouthpiece 130. The mouthpiece 130 can be a separable component of the vaporizer cartridge 120 or can be integrally formed with other component(s) of the vaporizer cartridge 120 (for example, formed as a unitary structure with the reservoir 140 and/or the like).

Figure 1F:
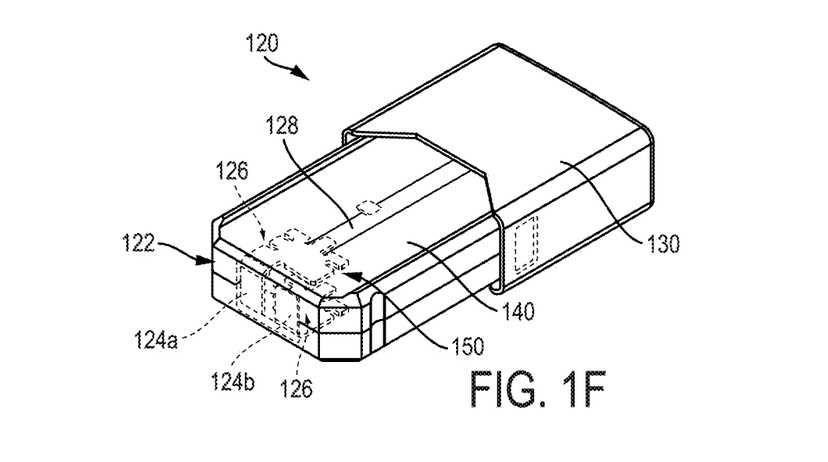

FIG. 1F shows additional features that can be included in the vaporizer cartridge 120 consistent with implementations of the current subject matter. For example, the vaporizer cartridge 120 can include a plurality of cartridge contacts (such as cartridge contacts 124a, 124b) disposed on the insertable end 122. The cartridge contacts 124a, 124b can optionally each be part of a single piece of metal that forms a conductive structure (such as conductive structure 126) connected to one of two ends of a resistive heating element. The conductive structure can optionally form opposing sides of a heating chamber and can act as heat shields and/or heat sinks to reduce transmission of heat to outer walls of the vaporizer cartridge 120. FIG. 1F also shows the cannula 128 within the vaporizer cartridge 120 that defines part of the airflow path 134 between the heating chamber formed between the conductive structure 126 and the mouthpiece 130.

As mentioned above, existing vaporizer devices can include an atomizer that is generally configured to heat vaporizable material into a vaporized material. The vaporized material is then combined with the primary airflow through the vaporizer device that flows across the atomizer to therefore generate an inhalable aerosol. As a result, the vaporizable material is heated, vaporized, and condensed within the atomizer. This can inhibit control of the condensation of the vaporized material independent of the primary airflow that travels through the device. Further, this design configuration forces the primary airflow to be the source of cool air for purposes of condensing the vaporized material. As such, as the cool primary airflow passes across the atomizer, the atomizer is cooled thereby resulting in heat loss. Under these circumstances, the effectiveness of the vaporizer device to vaporize a desired amount of vaporizable material, such as when a user takes a puff on the vaporizer device, can be reduced. Various features and devices are described below that improve upon or overcome these issues.

The vaporizer cartridges described herein allow for primary condensation of the vaporized material to occur outside of the atomizer. That is, the vaporizer cartridges are configured to delay nucleation of the vaporized material, which would typically occur in the atomizer, so as to gain more control over the resulting particle size. Further, in forcing nucleation downstream of the atomizer, faster cooling of the vaporized material can be achieved, thereby producing an aerosol with smaller and possibly more uniformly sized particles. As used herein, "nucleation" refers to the initial formation of a new thermodynamic phase or a new structure (e.g., via self-assembly and/or self-organization). For example, the nucleation of the vaporized material can refer to the primary condensation of the vaporized material in which at least a portion of the vaporized material in the gas phase condenses to form aerosol particles.

The vaporizer cartridges generally include a channeled configuration in which a stream of vaporized material produced by an atomizer is combined downstream with primary airflow through the cartridge at a junction (e.g., a T-junction). At this junction, the vaporized material is substantially cooled by the primary airflow and thereby condenses to form an inhalable aerosol.

Figure 2:
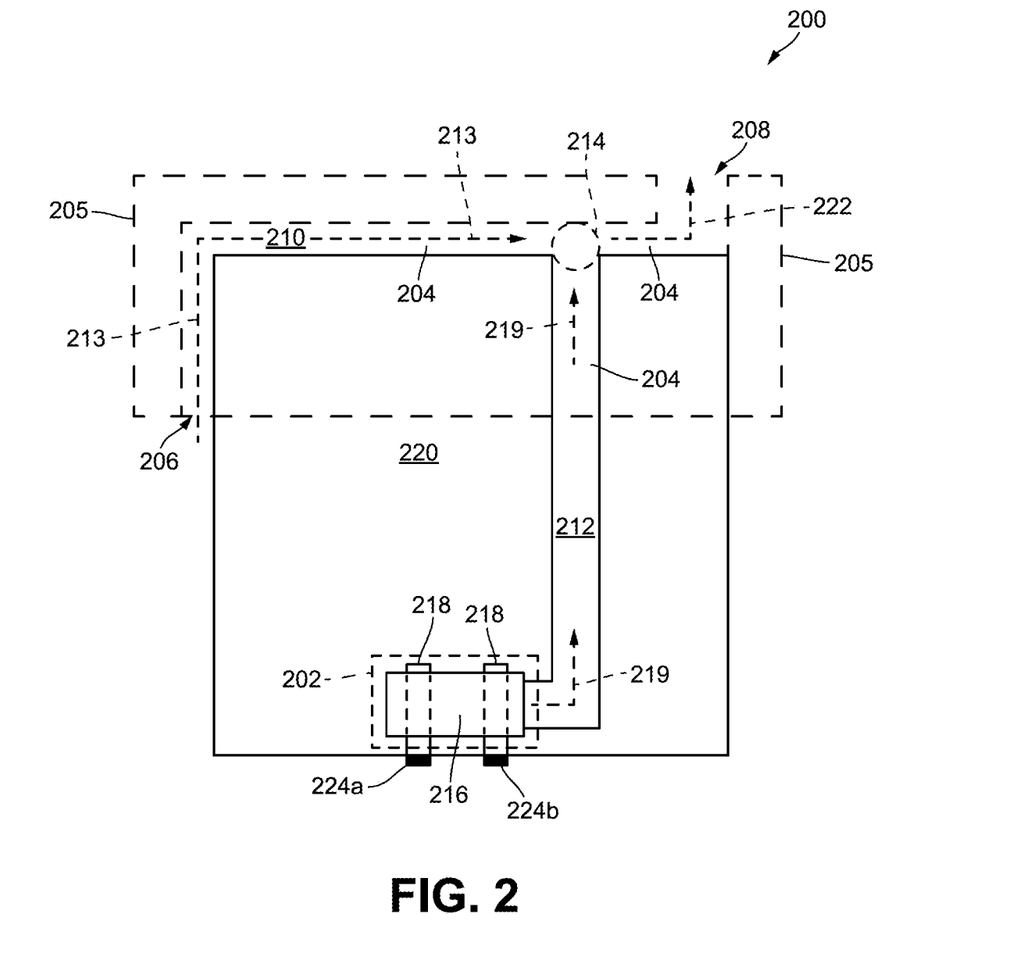

FIG. 2 illustrates an exemplary vaporizer cartridge 200 that can be selectively coupled to and removable from a vaporizer body, such as vaporizer body 110 shown in FIGS. 1A-1D. More specifically, the vaporizer cartridge 200 includes an atomizer 202 and a channel 204 that is configured to extend through the vaporizer cartridge 200 from an inlet 206 to an outlet 208. The channel 204 includes an airflow path 210 and a vapor path 212 that intersect at a first junction 214 between the inlet 206 and the outlet 208. The airflow path 210 is configured to receive and substantially allow air, illustrated as dashed-line arrow 213, to pass therethrough, for example as a user puffs on a mouthpiece 205 coupled with the vaporizer cartridge 200. For purposes of simplicity, certain components of the vaporizer cartridge 200 are not illustrated.

While the atomizer 202 can have a variety of configurations, the atomizer 202, as shown in FIG. 2, includes a wicking element 216 and a heating element 218. The wicking element 216 can be configured to substantially draw a vaporizable material (not shown) from a reservoir 220 and into the atomizer 202. The heating element 218 can be configured to substantially vaporize the vaporizable material into a vaporized material, illustrated as dashed-lined arrow 219. Exemplary embodiments of suitable wicking and heating elements are discussed above.

As shown, the atomizer 202 is in communication with the vapor path 212 so that the vaporized material 219 can flow into the vapor path 212. The vapor path 212 is configured to direct the vaporized material 219 into the first junction 214 so that the vaporized material 219 can mix with the air 213 to result in formation of an aerosol, illustrated as dashed-lined arrow 222, downstream of the atomizer 202.

The vapor path 212 can have a variety of shapes and sizes. For example, as shown in FIG. 2, the vapor path 212 extends from the atomizer 202 and intersects with the airflow path 210 at the first junction 214. As such, during use, the vaporized material 219 travels through the vapor path 212 and combines with the air 213 at the first junction 214, and as a result, the vaporized material 219 substantially condenses into aerosol 222 that is subsequently inhaled by a user through the outlet 208 and thus the mouthpiece 205. While the first junction 214 can have a variety of configurations, the first junction 214, as shown in FIG. 2, is a T-junction in which the vapor path 212 intersects the airflow path 210 orthogonally (e.g., at approximately 90° angle). Other configurations, including other variations of three-way junctions between the vapor path 212 and the airflow path 210, are also contemplated herein.

In some embodiments, the vaporizer cartridge 200 includes two or more cartridge contacts such as, for example, a first cartridge contact 224a and a second cartridge contact 224b. The two or more cartridge contacts can be configured to couple, for example, with the receptacle contacts 125a and 125b in order to form one or more electrical connections with the vaporizer body 110. The circuit completed by these electrical connections can allow delivery of electrical current to the heating element 218 in the atomizer 202. The circuit can also serve additional functions such as, for example, measuring a resistance of the heating element 218 for use in determining and/or controlling a temperature of the heating element 218 based on a thermal coefficient of resistivity of the heating element 218.

In some embodiments, the airflow path can include two or more segments that can be configured to divert portions of the air from the airflow path to other areas of the vaporizer cartridge. For example, one or more portions of diverted air can be used to help transport the vaporized material to the first junction.

Figure 3:
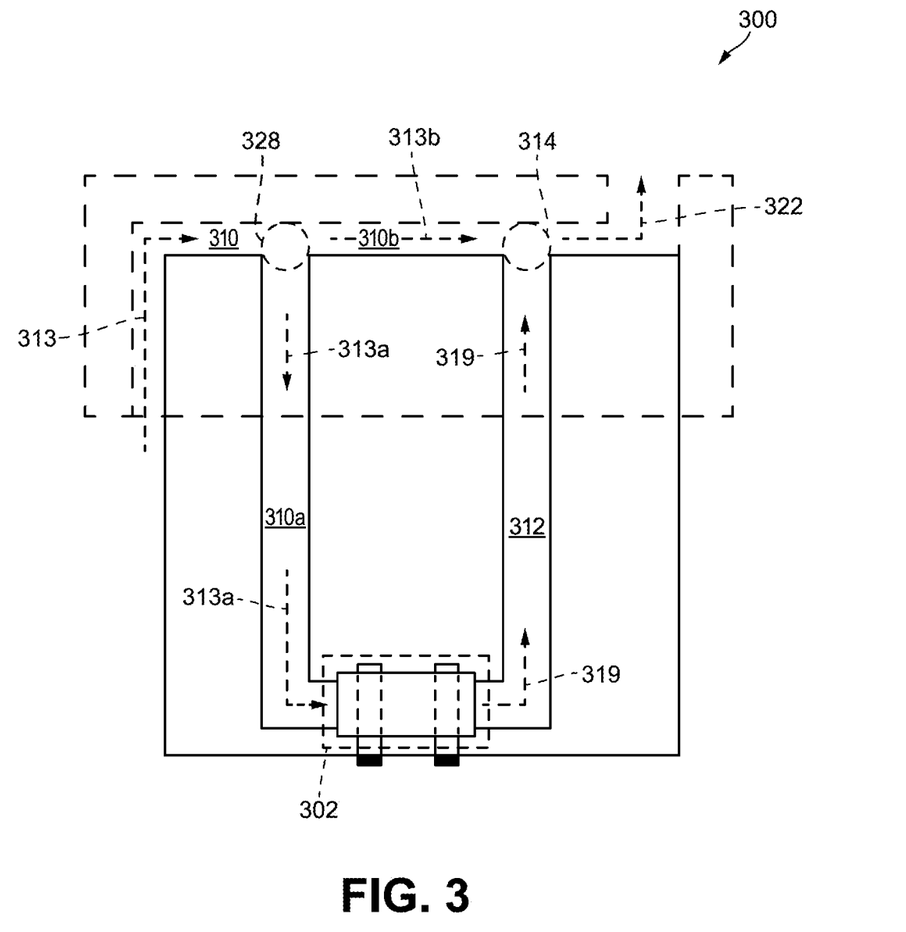

FIG. 3 illustrates another exemplary vaporizer cartridge 300 that can be selectively coupled to and removable from a vaporizer body, such as vaporizer body 110 shown in FIGS. 1A-1D. Aside from the differences described below, the vaporizer cartridge 300 can be similar to vaporizer cartridge 200 (FIG. 2) and therefore similar features are not described in detail herein.

As shown, at a second junction 328 that is upstream of the first junction 314, the airflow path 310 diverges into a first airflow path segment 310a and a second airflow path segment 310b. While the first and second airflow path segments 310a, 310b can have a variety of configurations, in this illustrated embodiment, at least a portion of the first and second airflow path segments 310a, 310b extend in orthogonal directions relative to each other from the second junction 328. During use, once the air 313 reaches the second junction 328, the air 313 diverts into a first portion of air, illustrated as a dash-lined arrow 313a, and a second portion of air, illustrated as a dash-lined arrow 313b. The first portion of air 313a enters into and travels through the first airflow path segment 310a and the second portion of air 313b travels through the second airflow path segment 310b to the first junction 314.

The first airflow path segment 310a is in communication with the atomizer 302. As such, during use, the first portion of air 313a flows through the atomizer 302. While the amount of air 313 that may travel through the first airflow path segment 310a, and consequently through the atomizer 302, can vary, any diverted portion of the air 313, such as the first portion of air 313a, is configured to substantially transport the vaporized material 319 from the atomizer 302 through the vapor path 312 and into the first junction 314. For example, the first portion of air 313a can have a first volume and the second portion of air 313b can have a second volume that is greater than the first volume. As such, the second junction 328 can be configured to substantially prevent the majority of the air 313 from being diverted into the first airflow path segment 310a. Thus, while a portion of the air 313 may be pass through the atomizer 302, the majority of condensation of the vaporized material 319 occurs at the first junction 314 to produce the aerosol 322.

Figure 4:
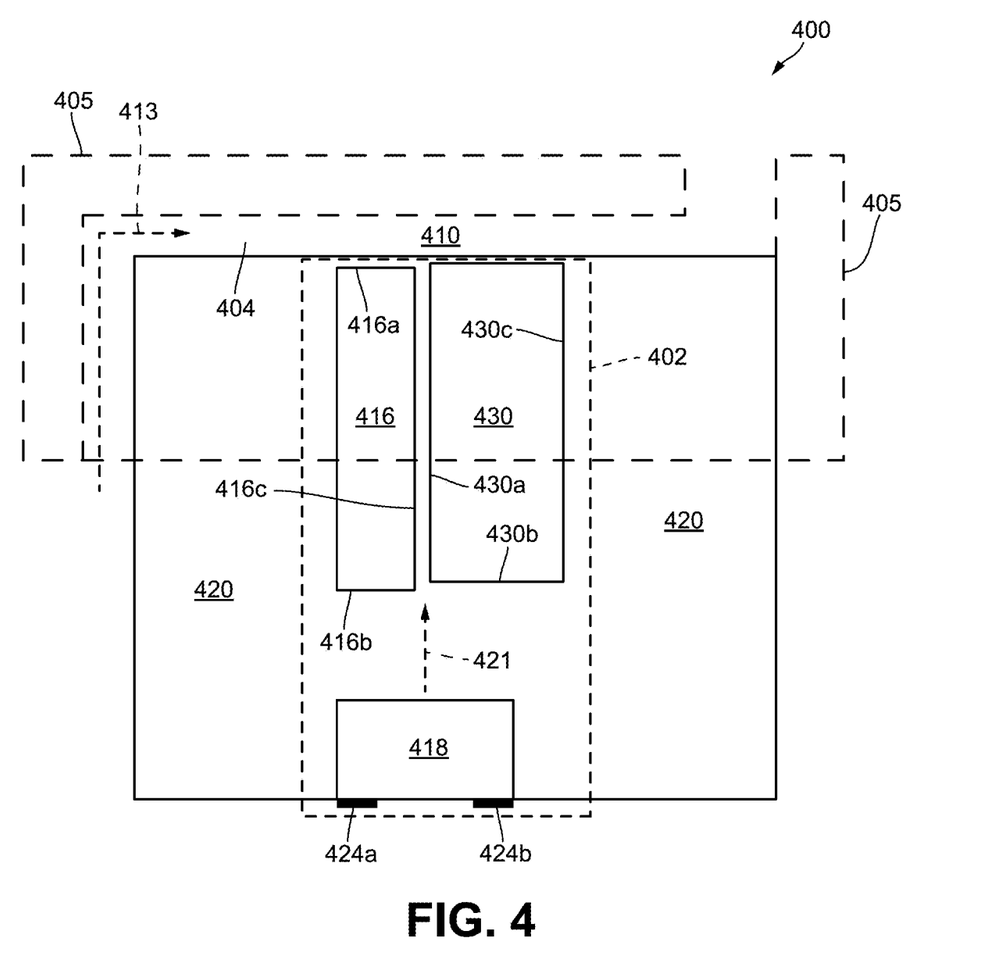

FIG. 4 illustrates another exemplary vaporizer cartridge 400 that can be selectively coupled to and removable from a vaporizer body, such as vaporizer body 110 shown in FIGS. 1A-1D. More specifically, the vaporizer cartridge 400 includes an atomizer 402 and an airflow channel 404 that defines an airflow path 410 that is configured to extend through the cartridge 400. The airflow path 410 is configured to receive and substantially allow air, illustrated as a dash-lined arrow 413, to pass therethrough, for example as a user puffs on a mouthpiece 405 coupled with the vaporizer cartridge 400. For purposes of simplicity, certain components of the vaporizer cartridge 400 are not illustrated.

While the atomizer 402 can have a variety of configurations, the atomizer 402, as shown in FIG. 4, includes a wicking element 416 and a heating element 418. The wicking element 416 can be configured to substantially draw a vaporizable material (not shown) from a reservoir 420 and into the atomizer 402. The wicking element 416 can extend from a first surface 416a to an opposing, second surface 416b. The first and second surfaces 416a, 416b can each extend substantially parallel to the airflow path 410, as shown in FIG. 4. The heating element 418 can be configured to vaporize the vaporizable material into a vaporized material. For example, the heating element 418 can direct heat, illustrated as dash-lined arrow 421, across a lateral surface 416c of the wicking element 416 so as to vaporize at least a portion of the vaporizable material within the wicking element 416 (e.g., at least the vaporizable material at the lateral surface 416c of the wicking element 416). As shown, the lateral surface 416c is interposed between a bulk of the wicking element 416 and a vapor chamber 430. Exemplary embodiments of suitable wicking and heating elements are discussed above.

The atomizer 402, as shown in FIG. 4, includes the vapor chamber 430 that is in communication with the wicking element 416 and the airflow channel 404. While the vapor chamber 430 can have a variety of configurations, the vapor chamber 430, as shown in FIG. 4, is defined by three walls 430a, 430b, 430c and is substantially rectangular in shape. In other embodiments, the vapor chamber 430 can have any other suitable shape.

The vapor chamber 430 can be configured to substantially allow at least a portion of the vaporized material to pass therethrough and into the airflow channel 404 so that the portion of the vaporized material mixes with the air 413 traveling through the airflow path 410 to form an aerosol outside of the atomizer 402. For example, the wall 430a, which, as shown in FIG. 4, is adjacent to the lateral surface 416c of the wicking element 416, can be formed of a permeable material. Alternatively, or in addition, the wall 430a can include one or more through holes that are configured to allow the vaporized material to substantially pass therethrough and into the vapor chamber 430.

The vapor chamber 430 can be positioned in a variety of locations within the atomizer 402. For example, as shown in FIG. 4, at least a portion of the vapor chamber 430 is bounded by the airflow channel 404. This portion of the vapor chamber 430 can be formed of a permeable material that is configured to allow the vaporized material to substantially pass therethrough and into the airflow path 410. Alternatively, or in addition, this portion of the vapor chamber 430 can be include at least one or more through holes that are configured to allow the vaporized material to substantially pass therethrough and into the airflow path 410.

In some embodiments, the vaporizer cartridge 400 includes two or more cartridge contacts such as, for example, a first cartridge contact 424a and a second cartridge 424b. The two or more cartridge contacts can be configured to couple, for example, with the receptacle contacts 125a and 125b in order to form one or more electrical connections with the vaporizer body 110. The circuit completed by these electrical connections can allow delivery of electrical current to the heating element 418 in the atomizer 402. The circuit can also serve additional functions such as, for example, measuring a resistance of the heating element 418 for use in determining and/or controlling a temperature of the heating element based on a thermal coefficient of resistivity of the heating element.

Figure 5:
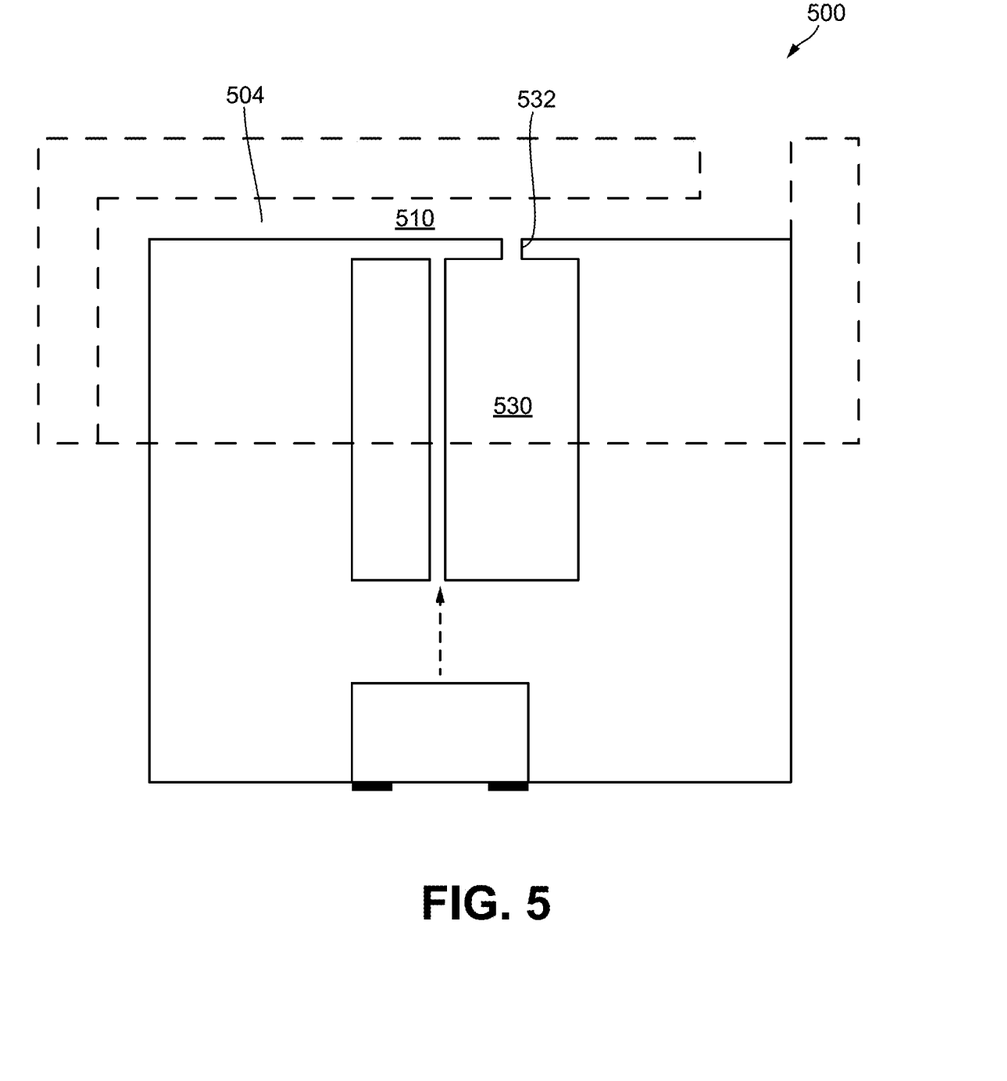

FIG. 5 illustrates another exemplary vaporizer cartridge 500 that can be selectively coupled to and removable from a vaporizer body, such as vaporizer body 110 shown in FIGS. 1A-1D. Aside from the differences described below, the vaporizer cartridge 500 can be similar to vaporizer cartridge 400 (FIG. 4) and therefore similar features are not described in detail herein.

In some embodiments, the vapor chamber 530 includes one or more vents extending between the vapor chamber 530 and the airflow channel 504. In the example shown in FIG. 5, the vapor chamber 530 includes a vent 532 configured to substantially direct the vaporized material from the vapor chamber 530 and into the airflow path 510. The vent 532 can have any size that is configured to substantially allow the vaporized material within the vapor chamber 530 to pass into the airflow path 510. In some embodiments, the velocity of the air flowing adjacent to the vent 532 can substantially create a pressure differential across the vent 532 and between the vapor chamber 530 and the airflow channel 504. For example, the velocity of the air flowing adjacent to the vent 532 can create an area of negative pressure in which the pressure in a first area of the airflow path 510 on one side of the vent 532 is lower than the pressure in a second area of the vapor chamber 530 on an opposite side of the vent 532. This pressure differential can draw vaporized material from the vapor chamber 530 through the vent 532 and into the airflow path 510.

Terminology

For purposes of describing and defining the present teachings, it is noted that unless indicated otherwise, the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present.

Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments and implementations only and is not intended to be limiting. For example, as used herein, the singular forms "a," "an," and "the" are intended to include the plural forms as well, unless the context clearly indicates otherwise.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

Spatially relative terms, such as "forward", "rearward", "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings provided herein.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the teachings herein. For example, the order in which various described method steps are performed may often be changed in alternative embodiments, and in other alternative embodiments, one or more method steps may be skipped altogether. Optional features of various device and system embodiments may be included in some embodiments and not in others. Therefore, the foregoing description is provided primarily for exemplary purposes and should not be interpreted to limit the scope of the claims.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example, as would a processor cache or other random access memory associated with one or more physical processor cores.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description. Use of the term "based on," herein and in the claims is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail herein, other modifications or additions are possible. In particular, further features and/or variations can be provided in addition to those set forth herein. For example, the implementations described herein can be directed to various combinations and subcombinations of the disclosed features and/or combinations and subcombinations of several further features disclosed herein. In addition, the logic flows depicted in the accompanying figures and/or described herein do not necessarily require the particular order shown, or sequential order, to achieve desirable results. Other implementations may be within the scope of the following claims.

What is claimed is:

1. A cartridge for a vaporizer device, the cartridge comprising:
    an atomizer that includes a wicking element that is configured to substantially draw a vaporizable material from a reservoir and into the atomizer, and a heating element that is configured to substantially vaporize the vaporizable material into a vaporized material; and
    a channel extending through the cartridge from an inlet to an outlet, the channel having an airflow path and a vapor path that intersect at a first junction between the inlet and the outlet, the airflow path being configured to receive and substantially allow air to pass therethrough;
    wherein the atomizer is in communication with the vapor path such that the vaporized material flows into the vapor path, and wherein the vapor path is configured to direct the vaporized material into the first junction so that the vaporized material mixes with the air to substantially form an aerosol downstream of the atomizer,
    wherein the airflow path includes a first airflow path segment and a second airflow path segment, and wherein the first airflow path segment is in communication with the atomizer, and wherein the first airflow path segment and the second airflow path segment intersect at a second junction that is upstream of the first junction, wherein the second junction diverts a first portion of the air into the first airflow path segment and across the atomizer, and wherein the second junction further diverts a second portion of the air towards the first junction.

2. The cartridge of claim 1, wherein the second junction is a T-junction.

3. The cartridge of claim 1, wherein the first portion of the air is configured to substantially transport the vaporized material from the atomizer and into the first junction.

4. The cartridge of claim 1, wherein the first portion of air has a first volume and the second portion of air has a second volume that is greater than the first volume.

5. The cartridge of claim 1, wherein a portion of the airflow path that is downstream of the first junction is configured to substantially allow the aerosol to pass therethrough and out of the channel.

6. The cartridge of claim 1, wherein the aerosol is substantially formed at the first junction.

7. The cartridge of claim 1, wherein the first junction is a T-junction.

8. A cartridge for a vaporizer device, the cartridge comprising:

an airflow channel that defines an airflow path that extends through the cartridge, the airflow path being configured to receive and substantially allow air to flow into and through the airflow channel; and an atomizer that includes a wicking element that is configured to substantially draw a vaporizable material from a reservoir and into the atomizer, a heating element that is configured to substantially vaporize the vaporizable material into a vaporized material, and a vapor chamber that is in communication with the wicking element and the airflow channel;

wherein the vapor chamber is configured to substantially allow at least a portion of the vaporized material to pass therethrough and into the airflow channel so that the portion of the vaporized material mixes with the air to form an aerosol outside of the atomizer, and wherein the wicking element extends from a first surface to an opposing second surface, and wherein the first surface and second surface each extend substantially parallel to the airflow path.

9. The cartridge of claim 8, wherein at least a portion of the vapor chamber is bounded by the airflow channel, and wherein the portion of the vapor chamber is formed of a permeable material that is configured to allow the vaporized material to substantially pass therethrough and into the airflow path.

10. The cartridge of claim 8, wherein the heating element directs heat across a lateral surface of the wicking element extending between the first and second surfaces.

11. The cartridge of claim 10, wherein the lateral surface is interposed between a bulk of the wicking element and the vapor chamber.

12. The cartridge of claim 8, wherein the vapor chamber includes at least one vent that extends between the vapor chamber and the airflow channel, and wherein the at least one vent is configured to substantially direct the vaporized material from the vapor chamber and into the airflow path.

13. The cartridge of claim 12, wherein a velocity of the air flowing adjacent to the at least one vent substantially creates a pressure differential across the at least one vent and between the vapor chamber and the airflow channel.

14. A vaporizer device, comprising:

a vaporizer body; and a cartridge that is selectively coupled to and removable from the vaporizer body, the cartridge including:

an atomizer that includes a wicking element that is configured to substantially draw a vaporizable material from a reservoir and into the atomizer, and a heating element that is configured to substantially vaporize the vaporizable material into a vaporized material, and a channel extending through the cartridge from an inlet to an outlet, the channel having an airflow path and a vapor path that intersect at a first junction between the inlet and the outlet, the airflow path being configured to receive and substantially allow air to pass therethrough;

wherein the atomizer is in communication with the vapor path such that the vaporized material flows into the vapor path, and wherein the vapor path is configured to direct the vaporized material into the first junction so that the vaporized material mixes with the air to substantially form an aerosol downstream of the atomizer, wherein the airflow path includes a first airflow path segment and a second airflow path segment, and wherein the first airflow path segment is in communication with the atomizer, and wherein the first air flow path segment and the second airflow path segment intersect at a second junction that is upstream of the first junction, wherein the second junction diverts a first portion of the air into the first airflow path segment and across the atomizer, and wherein the second junction further diverts a second portion of the air towards the first junction.

15. The device of claim 14, wherein the vaporizer body includes a power source.

* * * * *